United States Patent
Franckowiak

(10) Patent No.: US 9,649,462 B2
(45) Date of Patent: May 16, 2017

(54) LARYNGEAL MASK ANCHORING DEVICE FOR EDENTULOUS PATIENTS

(71) Applicant: Melissa Franckowiak, Grand Island, NY (US)

(72) Inventor: Melissa Franckowiak, Grand Island, NY (US)

( * ) Notice: Subject to any disclaimer, the term of this patent is extended or adjusted under 35 U.S.C. 154(b) by 15 days.

(21) Appl. No.: 14/641,523

(22) Filed: Mar. 9, 2015

(65) Prior Publication Data

US 2016/0263336 A1 Sep. 15, 2016

(51) Int. Cl.
*A61M 16/00* (2006.01)
*A61M 16/04* (2006.01)
*A61M 16/08* (2006.01)

(52) U.S. Cl.
CPC .... *A61M 16/0497* (2013.01); *A61M 16/0409* (2014.02); *A61M 16/0447* (2014.02); *A61M 16/0816* (2013.01); *A61M 2209/06* (2013.01)

(58) Field of Classification Search
CPC .............. A61M 16/04; A61M 16/0402; A61M 16/0427; A61M 16/0463; A61M 16/0488–16/0497; A61M 16/06; A61M 16/0605; A61M 16/06083; A61F 5/56; A61F 5/566; A61F 2005/563
See application file for complete search history.

(56) References Cited

U.S. PATENT DOCUMENTS

| | | | |
|---|---|---|---|
| 3,543,751 A | 12/1970 | Sheffer | |
| 4,449,526 A | 5/1984 | Elam | |
| 5,069,206 A * | 12/1991 | Crosbie | 128/207.17 |
| 5,529,582 A | 6/1996 | Fukuhara | |
| 2003/0015198 A1* | 1/2003 | Heeke | A61F 5/566 128/204.18 |
| 2008/0230055 A1* | 9/2008 | NaPier | 128/200.26 |
| 2012/0041440 A1* | 2/2012 | Tong et al. | 606/60 |

OTHER PUBLICATIONS

Kenneth N. Stevens, Acoustic Phoenetics, 2000, MIT Press, p. 25, table 1.1.*

* cited by examiner

*Primary Examiner* — Peter S Vasat
*Assistant Examiner* — Ned T Heffner
(74) *Attorney, Agent, or Firm* — Vincent G. LoTempio; Kloss, Stenger & LoTempio; David T. Stephenson

(57) ABSTRACT

A laryngeal mask anchoring device serves to seat an airway tube in an operational position against edentulous gums and the roof of the mouth to securely hold the airway tube in a desired position. The device also guides the airway tube towards the lungs, and braces the mouth open for manipulations to the airway tube. The device collapses into a substantially flat configuration for storage and portability. An upper and lower brace directly engage the edentulous gums. The braces are substantially smooth and pliable, and are configured to mate with substantially smooth, bald gums. A supportive platform with a slightly curved surface forms a supportive brace to hold the airway tube into place against the roof of the mouth. The slightly curved configuration of the platform nestles the airway tube, and the large surface area presses the airway tube against the roof of the mouth.

20 Claims, 3 Drawing Sheets

LARYNGEAL MASK ANCHORING DEVICE FOR EDENTULOUS PATIENTS

FIELD OF THE INVENTION

The present invention relates generally to a laryngeal mask anchoring device for edentulous patients. More so, a laryngeal mask anchoring device serves to seat an airway tube from a laryngeal mask in an operational position against edentulous gums to maintain the position of the airway tube passing through the mouth, while also partially separating to collapse into a substantially flat configuration for storage and portability.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known that a laryngeal mask enables anesthetists to channel oxygen or anesthesia gas to a patient's lungs during surgery. Generally, the laryngeal mask has an airway tube that connects to an elliptical mask with a cuff. During surgery, the mask may be pushed though the throat to the space between the vocal cords. When the cuff is inflated, the mask conforms to the anatomy with the bowl of the mask facing the space between the vocal cords. After correct insertion, the tip of the laryngeal mask sits in the throat against the muscular valve that is located at the upper portion of the esophagus.

It is known that there is great difficulty in providing air to the lungs during surgery. The skillset may require invasive procedures. These include varying levels of sedation given to patients while maintaining an open airway for spontaneously breathing patients and passing a gas through the throat to allow ventilation in the obtunded and apneic patient. There are a myriad of airway devices to support these skills, all by creating a physical passageway to the hypopharynx and tracheal opening or through the trachea. None of these devices are tolerated by an awake or moderately sedated patient because they touch areas of the hypopharynx that elicit a powerful gagging and coughing reaction.

Often, the medical professional who is responsible for forming the airway through the mouth and throat areas must utilize maneuvers to allow the air passage to be maintained in the obtunded patient. Beside head and neck positioning, these chin lift and jaw thrust maneuvers take advantage of the unique anatomy of the human temporo-mandibular joint and stretch the soft tissues to form the desired airway passage. Typically, in these maneuvers, the mouth is not opened except through the pulling of the chin or pushing the angle of the jaw. Also, the cam joint action is engaged, the hypopharynx is opened, and the air passage from the nose though the pharynx can be created. These maneuvers often take away from the chief surgical procedures.

It is known that edentulism is the condition of being toothless to at least some degree. When an individual's mouth is at rest, the teeth in the opposing jaws are nearly touching. This causes the formation of a freeway space of roughly 2-3 mm. However, this distance is partially maintained as a result of the teeth limiting any further closure past the point of maximum intercuspation. When there are no teeth present in the mouth, the natural vertical dimension of occlusion is lost and the mouth has a tendency to overdose. This may be problematic when trying to introduce air into the lungs with a laryngeal mask.

It is understood by those skilled in the art that because the laryngeal mask slides around and does not seat properly in edentulous patients, time can be lost trying to manipulate the laryngeal mask. It frequently has to be taped to the face, which can excoriate the skin and cause injury. The excessive movement also blocks the opening in the mouth, which further reduces air intake by the patient. Thus, an anchor for the laryngeal mask would allow for better ventilation while retaining the laryngeal mask in the proper position through the mouth.

Other proposals have involved for introducing air into the passage and securely holding the laryngeal mask in a desired orientation, especially for am edentulous mouth. The problem with these devices is that they do not provide a stable enough platform for anchoring the airway tube; nor do these devices attach to edentulous gums securely.

Thus, an unaddressed need exists in the industry to address the aforementioned deficiencies and inadequacies. Even though the above cited methods for a laryngeal mask anchoring device and related maneuvers meets some of the needs of the market, an anchoring device designed to securely seat an airway tube to an edentulous mouth, guide an airway tube towards the lungs, at least partially brace open the mouth for enhanced ventilation, and collapse for storage and portability of the device is still desired.

SUMMARY OF THE INVENTION

The present invention is directed to a laryngeal mask anchoring device that serves to anchor an airway tube from a laryngeal mask in an operational position against edentulous gums and the roof of the mouth in order to seat the airway tube in a desired position in and around the toothless mouth. The anchoring device also serves to guide the airway tube towards the lungs, and brace the mouth open for manipulations to the airway tube and other surgical maneuvers. After operational use, the anchoring device partially separates at designated points to collapse into a substantially flat configuration for storage and portability. In essence, the anchoring device is specially designed to enable facilitated operation of the laryngeal mask in an edentulous patient.

In some embodiments, the laryngeal mask anchoring device is configured to anchor a laryngeal mask against edentulous gums to maintain the position of an airway tube passing through the mouth, while also separating in some sections to collapse into a substantially flat configuration for storage and portability. The anchoring device seats the airway tube in the desired orientation in the mouth, such that the laryngeal mask remains in position during use, and the ventilation for the patient is improved as the edentulous mouth is at least partially braced open. In this manner, ancillary fasteners and bracing components are not required to hold the laryngeal mask and airway tube in the desired position through the mouth.

The anchoring device comprises various components that create a synergy with the toothless gums, such that the airway tube is seated properly on the edentulous gums. For one, an upper and lower brace that directly engage the edentulous gums are substantially smooth and pliable, and are configured to mate with substantially smooth, bald gums. This forms a better fit against the bald gums. The braces also have a deep upper and lower channel, respectively, that is effective for securely receiving the often slippery edentulous gums more firmly. Additionally, a supportive rigid platform with a slightly curved surface forms a supportive brace to hold the airway tube into place against the roof of the mouth. The slightly curved configuration of the platform nestles the airway tube, and the large surface area serves to press the airway tube against the roof of the mouth.

In some embodiments, the anchoring device also serves to guide the airway tube towards the lungs, while also bracing the mouth open for orientation of the airway tube and other surgical maneuvers. The anchoring device is configured to mate with the upper and lower gums of the mouth, including an edentulous mouth. The device locks into an operational configuration that conforms to the gums for functionality with the airway tube, and unlocks to separate its components for forming a substantially flat configuration for portability and storage.

The anchoring device comprises an upper brace and lower brace designed to affix onto gums that may have substantially no teeth, such as an edentulous mouth. The substantially smooth and pliable configuration of the braces is efficacious for engaging the edentulous gums. The braces are configured to conform to the generally U-shaped disposition of the gums, partially forming a seal with the gums. The upper and lower braces are stacked in conformation with the general disposition of the upper and lower gum, and have sufficient flexibility to articulate with movements by the jaw.

In some embodiments, a platform may extend from the upper brace, orienting towards the throat. The platform may have a slightly curved configuration to funnel the airway tube towards the lungs while preventing the airway tube from falling off the platform. This serves as a planar brace to anchor the airway tube accordingly. Furthermore, the platform is sufficiently broad so as to provide surface on which the airway tube can brace against. In one embodiment, the platform extends from the upper brace on the gums to the upper portion of the throat, proximal to the laryngeal prominence. However, in other embodiments, the platform may protrude deeper into the throat.

In some embodiments, the anchoring device is collapsible into a substantially flat configuration for facilitated storage and portability. The upper and lower brace are operationally locked into the stacked configuration through a locking mechanism that supports the braces, yet is sufficiently flexible to enable the jaw to move freely. A flexible lock strip extends between the upper and lower brace from the sides of the upper and lower brace to maintain the anchoring device in the operational configuration. The upper and lower braces can be unlocked from each other by detaching a locking end of the lock strip from the lower brace and/or the upper brace. In one embodiment, the locking mechanism comprises a groove in the lower brace and a shaped protrusion in the lock end of the lock strip that engage and disengage in a frictional snap lock communication.

A flexible connector extends between the braces on the opposite side of the braces not having the lock strip. The connector may permanently attach to both the upper and lower brace. Once unlocked at the lock end of the lock strip, the braces may pivot laterally around the connector and collapse into a generally flat configuration. The braces pivot to the same parallel plane. The platform, which is substantially flat, follows the upper brace into this collapsed configuration.

A first aspect of the present invention provides an anchoring device for seating an airway tube against edentulous gums during operation and collapsing into a storable configuration while nonoperational, comprising:

an upper brace defined by a substantially U-shaped upper channel having a substantially smooth, pliable surface, the upper brace further defined by an upper front section, an upper rear section, and a pair of upper sides;

a lower brace disposed oppositely the upper brace, the lower brace defined by a substantially U-shaped lower channel having a substantially smooth, pliable surface, the lower brace further defined by a lower front section, a lower rear section, and a pair of lower sides;

a platform defined by a slightly curved planar surface, the platform disposed to extend from the upper front section towards the upper rear section;

a connector defined by a substantially flexible composition, the connector disposed to join the upper brace and the lower brace at the respective upper and lower sides; and a lock strip defined by a substantially flexible composition, the lock strip further defined by a locking end and an integrated end, the integrated end disposed to join the upper brace or the lower brace at the respective upper or lower sides, the locking end configured to detachably join the upper brace or the lower brace at the respective upper or lower sides, wherein the anchoring device is operational when the locking end is attached to the upper brace or the lower brace, wherein the anchoring device is substantially flat and nonoperational when the locking end is detached from the upper brace or the lower brace.

In a second aspect of the present invention, the anchoring device is configured to operate with a laryngeal mask for anchoring an airway tube to edentulous gums, guiding the airway tube from the general proximity of the mouth towards the direction of the lungs, and at least partially bracing the mouth open for enhanced ventilation.

In another aspect, the upper channel is configured to receive an edentulous upper gum.

In another aspect, the pair of upper sides are disposed to extend between the upper front section and the upper rear section.

In another aspect, the lower channel is configured to receive an edentulous lower gum.

In another aspect, the pair of lower sides are disposed to extend between the lower front section and the lower rear section.

In another aspect, the platform is configured to curve in a concave shape for enhanced support of the airway tube.

In another aspect, the platform comprises a platform front end and a platform rear end.

In another aspect, the platform has a length about 2 to 6 inches.

In yet another aspect, the connector is configured to fold between the upper brace and the lower brace.

In yet another aspect, the locking end of the lock strip detachably joins the lower brace.

In yet another aspect, the locking end of the lock strip comprises a shaped protrusion.

In yet another aspect, the shaped protrusion comprises a T-shape.

In yet another aspect, the lower brace comprises a groove configured to mate with the shaped protrusion.

In yet another aspect, the shaped protrusion and the groove form a frictional snap locking configuration.

In yet another aspect, the lower brace and the upper brace are configured to pivot laterally around the connector, and onto the same plane when the locking end detaches from the lower brace.

In yet another aspect, the lower brace and the upper brace are configured to laterally pivot onto the substantially same plane when the locking end detaches from the lower brace.

In yet another aspect, the connector and the lock strip are configured to compress into a substantially flat configuration when the upper brace and the lower brace are detached at the locking end.

In yet another aspect, the anchoring device comprises a pliable silicone or a plastic composition.

It is one objective to provide an anchoring device that is operable with a laryngeal mask and fits into an edentulous mouth.

Yet another objective is to provide an upper brace and a lower brace that pivot laterally around a connector and compress into a substantially flat configuration for storage.

Yet another objective is to provide a platform that is sufficiently curved so as to support the airway tube without allowing the tube to fall of the edges of the platform.

Yet another objective is to provide a flexible lock strip and connector that can compress into a substantially flat configuration.

Yet another objective is to provide a locking mechanism that easily detaches and is not obstructive to the cheeks.

Yet another objective is to provide an anchoring device for a laryngeal mask that is inexpensive to produce and easy to install in the mouth.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The present invention and the manner in which it may be practiced is further illustrated with reference to the accompanying drawings wherein.

Like reference numerals refer to like parts throughout the various views of the drawings.

DETAILED DESCRIPTION OF THE INVENTION

Figures 1, 2:
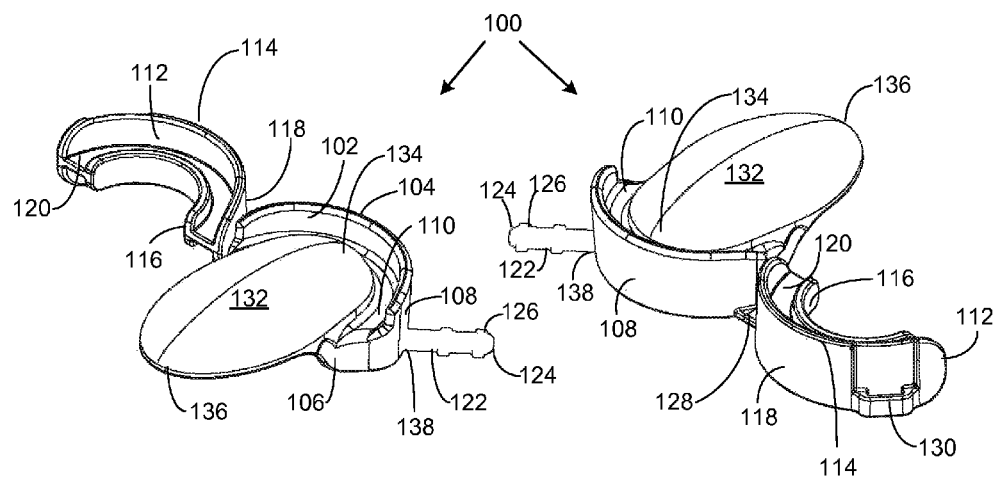
FIG. 1. is a rear perspective view of an exemplary laryngeal mask anchoring device, in accordance with an embodiment of the present invention.
FIG. 2. is a front perspective view of an exemplary laryngeal mask anchoring device, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. §112.

In one embodiment of the present invention, presented in FIGS. 1-8, a laryngeal mask anchoring device 100 serves to seat an airway tube (not shown) from a laryngeal mask (not shown) in an operational position against edentulous gums (not shown) to maintain the position of the airway tube passing through the mouth. The anchoring device 100 also supports the airway tube against the edentulous gums and the roof of the mouth, such that the airway tube is firmly positioned for operation and accurately guided through the mouth and towards the lungs. The anchoring device 100 also forms a brace for the jaws, at least partially bracing the mouth open for orientation of the airway tube and other surgical maneuvers. After operational use, the anchoring device 100 partially separates at designated points to collapse into a substantially flat configuration for storage and portability. In essence, the anchoring device 100 is specially designed to enable facilitated operation of the laryngeal mask in an edentulous patient.

In some embodiments, the anchoring device 100 seats the airway tube in the desired orientation in the mouth, such that the laryngeal mask remains in position during use, and the ventilation for the patient is improved as the mouth is at least partially braced open. Because the anchoring device 100 seats so naturally and securely in the edentulous mouth, ancillary fasteners and bracing components are not required to hold the laryngeal mask and airway tube in the desired position through the toothless mouth.

The anchoring device 100 comprises various components that create a synergy with the edentulous gums, such that the airway tube is seated properly on the edentulous gums. For one, an upper brace 102 and a lower brace 112 directly engage the edentulous gums. The braces 102, 112 are substantially smooth and pliable, thus having a surface that is effective for mating with the substantially smooth, bald gums. This forms a better fit against the bald gums. The braces 102, 112 also have a deep upper and lower channel 110, 120, respectively, that is effective for securely receiving the often slippery edentulous gums more firmly. Additionally, a supportive rigid platform 132 with a slightly curved surface forms a supportive brace to hold the airway tube into place against the roof of the mouth. The slightly curved configuration of the platform 132 nestles the airway tube, and the large surface area serves to press the airway tube against the roof of the mouth.

The anchoring device 100 is configured to form a snug mating surface with the upper and lower gums of the mouth, such that minimal movement of the mouth, head, chin, or neck is allowed. In some embodiments, the anchoring device 100 may be efficacious for fitting into an edentulous mouth. However, in other embodiments, the anchoring device 100 may be configured to engage partial teeth, dental implants, dentures, and uneven edentulous gums. Additionally, the anchoring device 100 is configurable between an operational position and a storage position. The anchoring device 100 locks into the operational configuration by engaging the edentulous gums and the airway tube, and separates sections of its components to compress into a substantially flat shape for portability and storage.

In one embodiment, the anchoring device 100 is operational with a laryngeal mask known in the art. For example, a laryngeal mask having an airway tube on a first end and a mask with an inflatable cuff on a second end. The airway tube may dispense air or anesthesia gas through the lips, past the gums, down the throat, and past the esophagus before finally channeling the air or anesthesia gas into the lungs. The anchoring device 100 serves to anchor and direct the airway tube from the first end, in the mouth and throat region, while simultaneously bracing the mouth in an open or partially open disposition. It is understood that the airway tube is guided at the second end through the mask, the vocal cords, and the chest passageway. Thus, in one embodiment, the anchoring device 100 maintains an open air passage to the hypopharynx without touching any part of the mouth but the dental arches and the anterior tongue.

As referenced in FIG. 1, the anchoring device 100 may include an upper brace 102 defined by a substantially U-shaped upper channel 110. The U-shape of the upper channel 110 is configured to substantially match the angle and length of an upper gum, including an edentulous gum. The substantially smooth and pliable configuration of the upper brace 102 is efficacious for engaging the similarly surfaced edentulous gums. The upper brace 102 is further defined by an upper front section 104, an upper rear section 106, and a pair of upper sides 108. The upper front section 104 aligns with the front of the gums, while the upper rear section 106 aligns with a back region of the gums. The pair of upper sides 108 extend between the upper front section 104 and the upper rear section 106.

The illustration in FIG. 2 shows the device 100 having a lower brace 112 oppositely disposed from the upper brace 102, and in a stacked configuration that generally aligns with the upper brace 102. The lower brace 112 is defined by a substantially U-shaped lower channel 120. The lower brace 112 may be configured to substantially match the angle and length of a lower gum, including an edentulous gum. The substantially smooth and pliable configuration of the lower brace 112 is efficacious for engaging the similarly surfaced edentulous gums. The lower brace 112 comprises a lower front section 114, a lower rear section 116, and a pair of lower sides 118 extending between the lower front section 114 and the lower rear section 116. The lower front section 114 aligns with the front of the gums, while the lower rear section 116 aligns with the back region of the gums. The pair of lower sides 118 extend between the lower front section 114 and the lower rear section 116.

In some embodiments, the braces 102, 112 are of sufficient size to slip easily over the upper or lower edentulous gum. The braces 102, 112 may conform to the generally U-shaped disposition of the gums, partially forming a seal with the edentulous gums. The generally flat surface of the braces 102, 112 may be effective for pressing against toothless gums. The upper and lower braces 102, 112 are stacked in conformation with the general disposition of the upper and lower gum, and have sufficient flexibility to articulate in conformance with movements by the jaw. The braces 102, 112 may be evenly spaced and thereby form enough of a gap to enable passage of a diameter sized for the airway tube.

Suitable materials for the braces 102, 112 may include, without limitation, a pliable silicone, a thermosetting plastic, a flexible polymer, and wood. In one alternative embodiment, an antimicrobial composition may be integrated into the upper and lower channels 110, 120. In one embodiment, the upper and lower braces 102, 112 are comprised of softenable and customizable materials that enables the respective channels 110, 120 to be size adjusted for variously sized gums and teeth, if applicable.

Figures 3, 4:
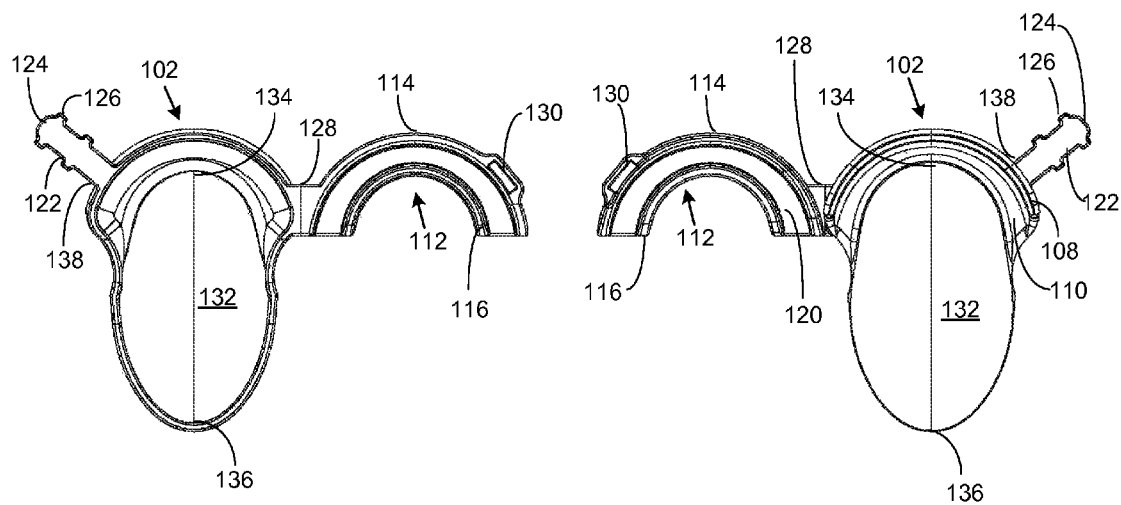
FIG. 3. is a bottom view of an exemplary laryngeal mask anchoring device, in accordance with an embodiment of the present invention.
FIG. 4. is a top view of an exemplary laryngeal mask anchoring device, in accordance with an embodiment of the present invention.

As shown in FIG. 3, the anchoring device 100 comprises a platform 132 that forms the surface area for support of the airway tube. The platform 132 is disposed to extend from the upper front section 104 towards the upper rear section 106 of the upper brace 102. However, in another embodiment, the platform 132 may extend from the lower brace 112. The platform 132 is defined by a slightly curved planar surface, having a generally concave shape. Those skilled in the art will recognize that movement by the head, the jaws, or the tongue may cause the airway tube to destabilize, especially during surgery. The concave shape and slight curvature nestles the airway tube onto the platform 132 so that it does not fall off the platform 132. The large surface area of the platform 132 serves to press the airway tube against the roof of the mouth. The platform's 132 unique shape also guides the airway tube towards the lungs.

Turning now to FIG. 4, the platform 132 may include a platform front end 134 and a platform rear end 136. The platform front end 134 is integrally formed with the upper rear section 106 of the upper brace 102. The platform rear end 136 provides the peripheral edge where the airway tube drops into the throat. In one embodiment, the platform 132 extends from the upper brace 102 on the gums to the upper portion of the throat, proximal to the laryngeal prominence. However, in other embodiments, the platform 132 may protrude deeper into the throat. The platform 132 may have a length between 2" to 6". Though other dimensions may be used, depending on the size of the mouth and the diameter of the airway tube.

Figure 5:
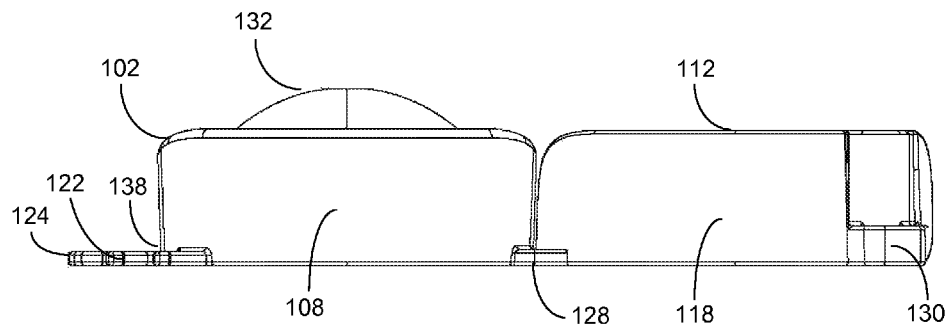
FIG. 5. is a frontal view of an exemplary laryngeal mask anchoring device, in accordance with an embodiment of the present invention.

As shown in FIG. 5, the anchoring device 100 may include a connector 128 that is disposed to join the upper brace 102 and the lower brace 112 at the respective upper and lower sides 108, 118. The connector 128 integrates with the upper and lower sides 108, 118 on the respective braces 102, 112 to form a permanent attachment. The connector 128 may form a generally U-shaped path between the upper and lower braces 102, 112. The connector 128 comprises a pliable composition that folds between the upper brace 102 and the lower brace 112 such that the device 100 may be compacted for storage and portability. Suitable materials for the connector 128 may include, without limitation, pliable silicone, soft plastic, and polymers.

The upper and lower brace 102, 112 may be operationally locked into the stacked configuration through a locking mechanism that supports the braces 102, 112, yet is sufficiently flexible to enable the jaw to move freely. A flexible lock strip 122 extends between the upper and lower braces 102, 112 from the sides 108, 118 to maintain the device 100 in the operational configuration. The lock strip 122 is defined by a locking end 124 and an integrated end 138 that engage the upper and lower sides 108, 118 of the braces 102, 112.

In some embodiments, the integrated end 138 joins with the upper brace 102 at either the left or right the upper side 108. The locking end 124 detachably joins the lower brace 112 at the left or right lower side 118. However, in other embodiments, either the integrated end 138 or the locking end 124 may join with either of the braces 102, 112. The upper and lower brace 102, 112 can be unlocked from each other by detaching the locking end 124 of the lock strip 122 from the lower brace 112. The lock strip 122 is defined by a substantially pliable composition, that folds between the upper brace 102 and the lower brace 112 such that the anchoring device 100 may be compacted for storage and portability.

Referring back to FIGS. 1 and 2, the locking end 124 comprises a locking mechanism that enables the locking end 124 to detach from the lower brace 112 (or the upper brace 102 if applicable). In one embodiment, the locking end 124 of the lock strip 122 comprises a shaped protrusion 126 that frictionally mates with a groove 130 in the lower side 118 of the lower brace 112. The shaped protrusion 126 may include a substantially T-shaped bar that slidably enters the groove 130 to lock into the lower brace 112. The mating engagement between the groove 130 and the shaped protrusion 126 forms a frictional snap locking configuration. This type of locking mechanism facilitates attachment and detachment of the lock strip 122 with one hand, especially while performing surgical maneuvers.

Figure 6:
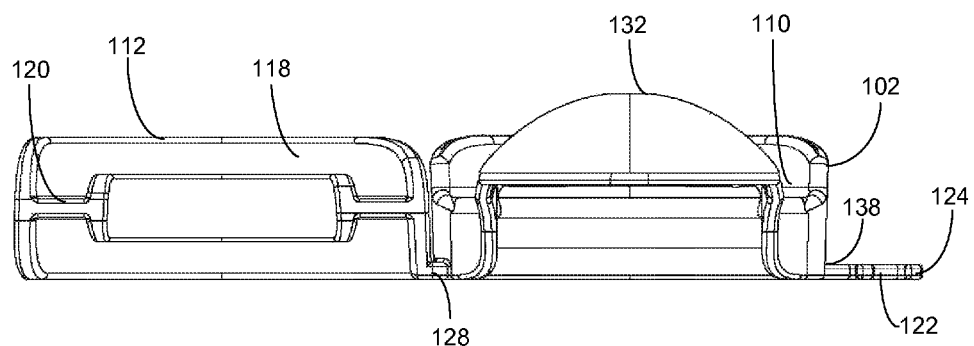
FIG. 6. is a rear view of an exemplary laryngeal mask anchoring device, in accordance with an embodiment of the present invention.
Figure 7:
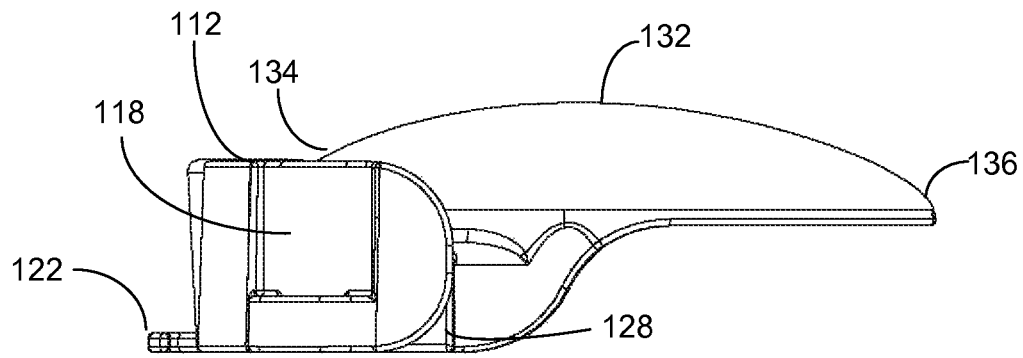
FIG. 7. is an elevated left side view of an exemplary laryngeal mask anchoring device, with an exemplary lower brace proximal, in accordance with an embodiment of the present invention.
Figure 8:
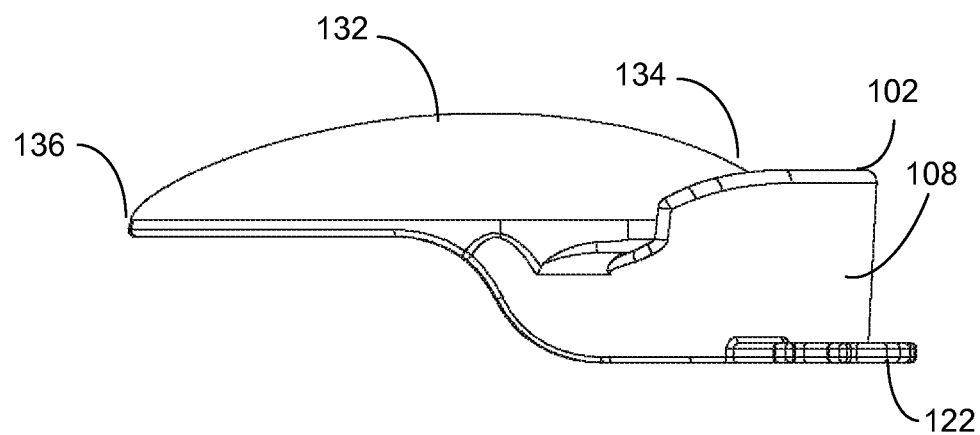
FIG. 8. is an elevated right side view of an exemplary laryngeal mask anchoring device, with an exemplary upper brace proximal, in accordance with an embodiment of the present invention.

FIG. 6 illustrates the result of detaching the locking end 124 of the lock strip 122 from the lower brace 112. Once the lock strip 122 is unlocked, the lower brace 112 and the upper brace 102 may pivot laterally relative to each other, with the connector 128 forming a pivot point of sorts. The upper and lower brace 102, 112 may pivot onto the same plane and away from the stacked configuration to a more planar, parallel disposition. From this parallel position the pliable construction of the connector 128 and the lock strip 122 may be compressed into a substantially flat configuration. The platform 132, which is substantially flat, follows the upper brace 102 into this collapsed configuration, such that the device 100 is flat and more easily stored or carried. Thus, the anchoring device 100 is operational when the locking end 124 is attached to the upper brace 102 or the lower brace 112. And the anchoring device 100 is substantially flat and nonoperational when the locking end 124 is detached from the upper brace 102 or the lower brace 112. FIGS. 7 and 8 illustrate both sides 108, 118 of the device 100 with the upper brace 102 and the lower brace 112 lying on the same plane in the flat, nonoperational configuration. In this configuration, the substantially pliable composition of the device 100 enables it to be compressed for storage and portability.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. An anchoring device for seating an airway tube against edentulous gums during operation and collapsing into a storable configuration while nonoperational, the device comprising:

an upper brace defined by a substantially U-shaped upper channel having a substantially smooth, pliable surface, the upper brace further defined by an upper front section, an upper rear section, and a pair of upper sides;

a lower brace disposed oppositely the upper brace, the lower brace defined by a substantially U-shaped lower channel having a substantially smooth, pliable surface, the lower brace further defined by a lower front section, a lower rear section, and a pair of lower sides; wherein there is an unobstructed and uniform open space between the upper brace and the lower brace;

an ovular platform defined by a slightly curved planar surface, the platform disposed to extend from a front of a mouth to a back of the mouth;

a connector defined by a substantially flexible composition, the connector disposed to join the upper brace and the lower brace at the respective upper and lower sides; and a resiliently bowable lock strip defined by a substantially flexible composition, wherein the resiliently bowable lock strip supports the upper and lower braces, maintains the anchoring device in an operational configuration, allows jaw movement, and accommodates various jaw sizes and shapes without requiring adjustment, wherein the lock strip is configured to reside inside the mouth during use, the lock strip being comprised of silicone and further defined by a locking end and an integrated end, the integrated end disposed to join the upper brace or the lower brace at the respective upper or lower sides, the locking end configured to detachably join the upper brace or the lower brace at the respective upper or lower sides, wherein the anchoring device is operational when the locking end is attached to the upper brace or the lower brace, wherein the anchoring device is substantially flat and nonoperational when the locking end is detached from the upper brace or the lower brace.

2. The device of claim 1, wherein the anchoring device is configured to operate with a laryngeal mask for anchoring an airway tube against edentulous gums, and guiding the airway tube from the general proximity of the mouth towards the direction of the lungs.

3. The device of claim 1, wherein the upper channel is configured to receive an edentulous upper gum.

4. The device of claim 1, wherein the pair of upper sides are disposed to extend between the upper front section and the upper rear section.

5. The device of claim 1, wherein the pair of lower sides are disposed to extend between the lower front section and the lower rear section.

6. The device of claim 1, wherein the platform is configured to curve in a concave shape for enhanced support of the airway tube.

7. The device of claim 1, wherein the platform comprises a platform front end and a platform rear end.

8. The device of claim 1, wherein the platform has a length about 2 to 6 inches.

9. The device of claim 1, wherein the connector is configured to fold between the upper brace and the lower brace.

10. The device of claim 1, wherein the locking end of the lock strip detachably joins the lower brace.

11. The device of claim 1, wherein the lower brace and the upper brace are configured to pivot laterally around the connector, and onto the same plane when the locking end detaches from the lower brace.

12. The device of claim 1, wherein the lower brace and the upper brace are configured to pivot onto the substantially same plane when the locking end detaches from the lower brace.

13. The device of claim 1, wherein the connector and the lock strip are configured to compress into a substantially flat configuration when the upper brace and the lower brace are detached at the locking end.

14. The device of claim 1, wherein the anchoring device comprises a pliable silicone or a plastic composition.

15. The device of claim 1, wherein the locking end of the lock strip comprises a shaped protrusion.

16. The device of claim 12, wherein, the shaped protrusion comprises a T-shape.

17. The device of claim 16, wherein the lower brace comprises a groove configured to mate with the shaped protrusion.

18. The device of claim 17, wherein the shaped protrusion and the groove form a frictional snap locking configuration.

19. Au anchoring device for seating an airway tube against edentulous gums during operation and collapsing into a storable configuration while nonoperational, the device comprising:
   an upper brace defined by a substantially U-shaped upper channel having a substantially smooth, pliable surface, the upper brace further defined by an upper front section, an upper rear section, and a pair of upper sides extending between the upper front section and the upper rear section;
   a lower brace disposed oppositely the upper brace, the lower brace defined by a substantially U-shaped lower channel having a substantially smooth, pliable surface, the lower brace further defused by a lower front section, a lower rear section, and a pair of lower sides extending between the lower front section and the lower rear section, the pair of lower sides comprising a groove; wherein, there is an unobstructed and uniform open space between the upper brace and the lower brace;
   an ovular platform defined by a slightly curved planar surface, the platform disposed to extend from a front of a mouth to a back of the mouth and further disposed to extend from an upper left section of the mouth to an upper right section of the mouth thereby substantially contacting an entirety of a roof of the mouth; further comprising a flexible convex surface to allow the device to conform to the roof of the mouth and a flexible concave surface to allow for space in the mouth beneath the platform;
   a connector defined by a substantially flexible composition, the connector disposed to join the upper brace and the lower brace at the respective upper and lower sides; and
   a lock strip defined by a substantially flexible composition, wherein the lock strip supports the upper and lower braces, maintains the anchoring device in an operational configuration, has sufficient flexibility to allow a jaw to open and close freely, and accommodates various jaw sizes and shapes without needing adjustment; wherein the lock strip is configured to reside inside the mouth during use, the lock strip further defined by a locking end and an integrated end, the integrated end disposed to join the upper brace or the lower brace at the respective upper or lower sides, the locking end configured to detachably join the upper brace or the lower brace at the respective upper or lower sides, the locking end comprising a shaped protrusion configured to form a frictional snap locking configuration with the groove,
   wherein the anchoring device is operational when the locking end is attached to the upper brace or the lower brace,
   wherein the anchoring device is substantially flat and nonoperational when the locking end is detached from the upper brace or the lower brace, and
   wherein the device is uniformly comprised of bulk pliable silicone that provides enough rigidity to brace the jaw open and enough flexibility to allow the device to conform to the roof of the mouth and allow the jaw to move freely.

20. An anchoring device for seating an airway tube against edentulous gums during operation and collapsing into a storable configuration while nonoperational, the device comprising:
   an upper brace defined by a substantially U-shaped upper channel having a substantially smooth, pliable surface, the upper brace further defined by an upper front section, an upper rear section, and a pair of upper sides;
   a lower brace disposed oppositely the upper brace, the lower brace defined by a substantially U-shaped lower channel having a substantially smooth, pliable surface, the lower brace further defined by a lower front section, a lower rear section, and a pair of lower sides; wherein there is an unobstructed and uniform open space between the upper brace and the lower brace;
   an ovular platform defined by a slightly curved planar surface, the platform disposed to extend from a front of a mouth to a back of the mouth and further disposed to extend from an upper left section of the mouth to an upper right section of the mouth thereby substantially contacting an entirety of a roof of the mouth; further comprising a flexible convex surface to allow the device to conform to the roof of the mouth and a flexible concave surface to allow for space in the mouth beneath the platform;
   a connector defined by a substantially flexible composition, the connector disposed to join the upper brace and the lower brace at the respective upper and lower sides; and
   a resiliently bowable lock strip defined by a substantially flexible composition, wherein the resiliently bowable lock strip supports the upper and lower braces, maintains the anchoring device in an operational configuration, allows jaw movement, and accommodates various jaw sizes and shapes without needing adjustment, wherein the lock strip is configured to reside inside the mouth during use, the lock strip further defined by a locking end and an integrated end, the integrated end disposed to join the upper brace or the lower brace at the respective upper or lower sides, the locking end configured to detachably join the upper brace or the lower brace at the respective upper or lower sides, wherein the anchoring device is operational when the locking end is attached to the upper brace or the lower brace, wherein the anchoring device is substantially flat and nonoperational when the locking end is detached from the upper brace or the lower brace.

* * * * *